United States Patent
Wolfe et al.

(10) Patent No.: US 6,799,070 B2
(45) Date of Patent: Sep. 28, 2004

(54) VOLTAGE CONTROL CIRCUITRY FOR CHARGING OUPUT CAPACITOR

(75) Inventors: James H. Wolfe, Canyon Country, CA (US); John C. Gord, Venice, CA (US); Joseph H. Schulman, Santa Clarita, CA (US)

(73) Assignee: The Alfred E. Mann Foundation for Scientific Research, Valencia, CA (US)

(*) Notice: Subject to any disclaimer, the term of this patent is extended or adjusted under 35 U.S.C. 154(b) by 429 days.

(21) Appl. No.: 10/056,848

(22) Filed: Jan. 23, 2002

(65) Prior Publication Data

US 2002/0068957 A1 Jun. 6, 2002

(51) Int. Cl.⁷ ............................................. A61N 1/36
(52) U.S. Cl. ......................................................... 607/7
(58) Field of Search .............................. 607/2, 7, 1, 3, 607/61, 72, 48, 50, 52, 59, 46; 600/554, 377; 363/59, 60, 65; 323/282; 307/38, 41

(56) References Cited

U.S. PATENT DOCUMENTS

| | | | |
|---|---|---|---|
| 5,193,539 A | 3/1993 | Schulman et al. | |
| 5,285,779 A | 2/1994 | Cameron et al. | |
| 5,324,316 A | * 6/1994 | Schulman et al. | ............. 607/61 |
| 5,418,751 A | 5/1995 | Kaiser | |
| 5,424,934 A | 6/1995 | Tanuma et al. | |
| 5,702,424 A | 12/1997 | Legay et al. | |
| 6,035,237 A | * 3/2000 | Schulman et al. | ............. 607/63 |

* cited by examiner

*Primary Examiner*—George Manuel
(74) *Attorney, Agent, or Firm*—Lee J. Mandell

(57) ABSTRACT

Battery driven voltage control circuitry charges an output capacitor, which periodically supplies a current pulse. The circuitry converts battery voltage VBAT to a charging voltage VUPC based upon programmed parameters and the voltage VCOMPL at the capacitor. The circuitry includes a voltage converter for multiplying VBAT to produce VUPC. VCOMPL is sampled to determine its "droop" at the end of an output current pulse. If the droop is lower than a threshold, then the voltage converter increases the charging voltage. If the droop is above a threshold, then the voltage converter reduces the charging voltage. This feedback maintains the output voltage within an acceptable operating range to produce an efficacious output current pulse for stimulation without causing unproductive energy loss. In order to avoid premature depletion of battery energy, VUPC is compared with VCOMPL to determine the optimum clock rate to be used to convert VBAT to VUPC.

16 Claims, 17 Drawing Sheets

VOLTAGE CONTROL CIRCUITRY FOR CHARGING OUPUT CAPACITOR

FIELD OF THE INVENTION

This invention relates generally to voltage control circuitry suitable for charging an output capacitor used to periodically supply an output current pulse. The invention is particularly suited for use in a battery powered device intended to be implanted in a patient's body for supplying a current pulse to stimulate body tissue.

BACKGROUND OF THE INVENTION

Implantable devices for stimulating body tissue are known in the prior art. For example, see U.S. Pat. No. 5,193,539 by Schulman, et al.; assigned to the same assignee as the present application. Such devices typically store energy in an output (or "stimulation") capacitor which is periodically discharged to supply an output current pulse to stimulate targeted tissue. The energy source primarily discussed in U.S. Pat. No. 5,193,539 for charging the capacitor is comprised of an external source for generating an alternating magnetic field. The alternating field energy is inductively coupled to an internal power supply circuit for producing a voltage for charging the stimulation capacitor. Unfortunately, such prior art devices require that a patient remain in very close proximity to the external source to enable the devices to continue to operate. For example, such devices are typically limited to operating for only several seconds to a minute or so without requiring additional energy from the external source.

More recent implantable devices have incorporated rechargeable batteries capable of operating for prolonged periods, in excess of one hour and up to many days, without requiring additional energy from an external power source. This difference in independent operating duration leads to a qualitative difference in the utility of the device and how effectively the devices can serve a patient.

In such battery operated implantable devices, it is very desirable to control the energy transfer from the battery to the output capacitor in a manner to minimize energy inefficiencies, i.e., unproductive energy losses, while also retaining the ability to control the amplitude, duration, and frequency of output current pulses supplied by the output capacitor to an impedance load, e.g., body tissue.

SUMMARY OF THE INVENTION

The present invention is directed to voltage control circuitry driven by a battery for producing a voltage for charging an output capacitor. The voltage control circuitry converts the battery voltage VBAT to a charging voltage VUPC based upon programmed parameters and the value of the output voltage VCOMPL measured at one terminal of the capacitor.

In many tissue stimulation applications, it may be medically efficacious to produce a high amplitude current across a high magnitude tissue impedance between output electrodes. This situation necessitates the application of a high amplitude charging voltage VUPC to the output capacitor. In accordance with the preferred embodiment, the voltage control circuitry includes an up/down voltage converter for deriving the charging voltage VUPC based on the battery voltage VBAT. The conversion can be implemented by known techniques including, for example, placing a plurality of converter capacitors in parallel across a voltage source for charging, and then switching the capacitors into a series configuration to produce a voltage equal to some multiple of the source voltage. Alternatively, the converter capacitors can first be placed in series across the voltage source and then switched to a parallel configuration to produce a voltage equal to some fractional value of the source voltage.

In accordance with the preferred embodiment, the output capacitor voltage is sampled at a specific point in time relative to each discharged current output pulse to generate the signal VCOMPL.

In accordance with a significant feature of the preferred embodiment, the charging voltage VUPC is compared with the output capacitor voltage VCOMPL to determine a clock rate used to convert VBAT to VUPC. For example, the clock rate can be off, slow, or fast depending upon the charge condition of the output capacitor. This feature is useful to conserve energy and avoid premature depletion of battery energy.

More particularly, in accordance with the preferred embodiment, the output voltage, sometimes referred to as the "compliance" voltage VCOMPL, is sampled to determine its final "droop" at the end of an output current pulse. If the final droop value is lower than a certain threshold ($\Delta V_{LOWER}$), then the voltage converter switches to increase the converter charging voltage VUPC. On the other hand, if the final droop value is above a certain threshold ($\Delta V_{UPPER}$), then the voltage converter switches to reduce the value of the voltage VUPC. This feedback action maintains the output capacitor voltage within an acceptable operating range to provide sufficient energy to produce an efficacious output current pulse for stimulation without causing unproductive energy loss, e.g., heat.

Exemplary embodiments of the invention intended for tissue stimulation are configured to be accommodated in a small implantable housing preferably having an axial dimension of less than 60 mm and a lateral dimension of less than 6 mm so as to be readily injectable. Devices in accordance with the invention preferably operate from a 2.4 to 4.5 V battery to provide stimulation output current pulses having a controllable amplitude of between 5 microamps and 20 milliamps, a controllable pulse width of between 10 microseconds and 2 milliseconds, a controllable repetition rate of between 1 pulse per second and 1000 pulses per second (pps).

BRIEF DESCRIPTION OF THE DRAWINGS

The above and other features and advantages of the invention will be more apparent from the following detailed description wherein:

FIG. 1c shows a block diagram of the voltage converter/clock control circuit of FIG. 1a;

FIG. 5 shows the different up/down converter states for each of the scale factors; FIG. 5 has seven parts, FIGS. 5a through 5g;

DETAILED DESCRIPTION

Figure 1A:
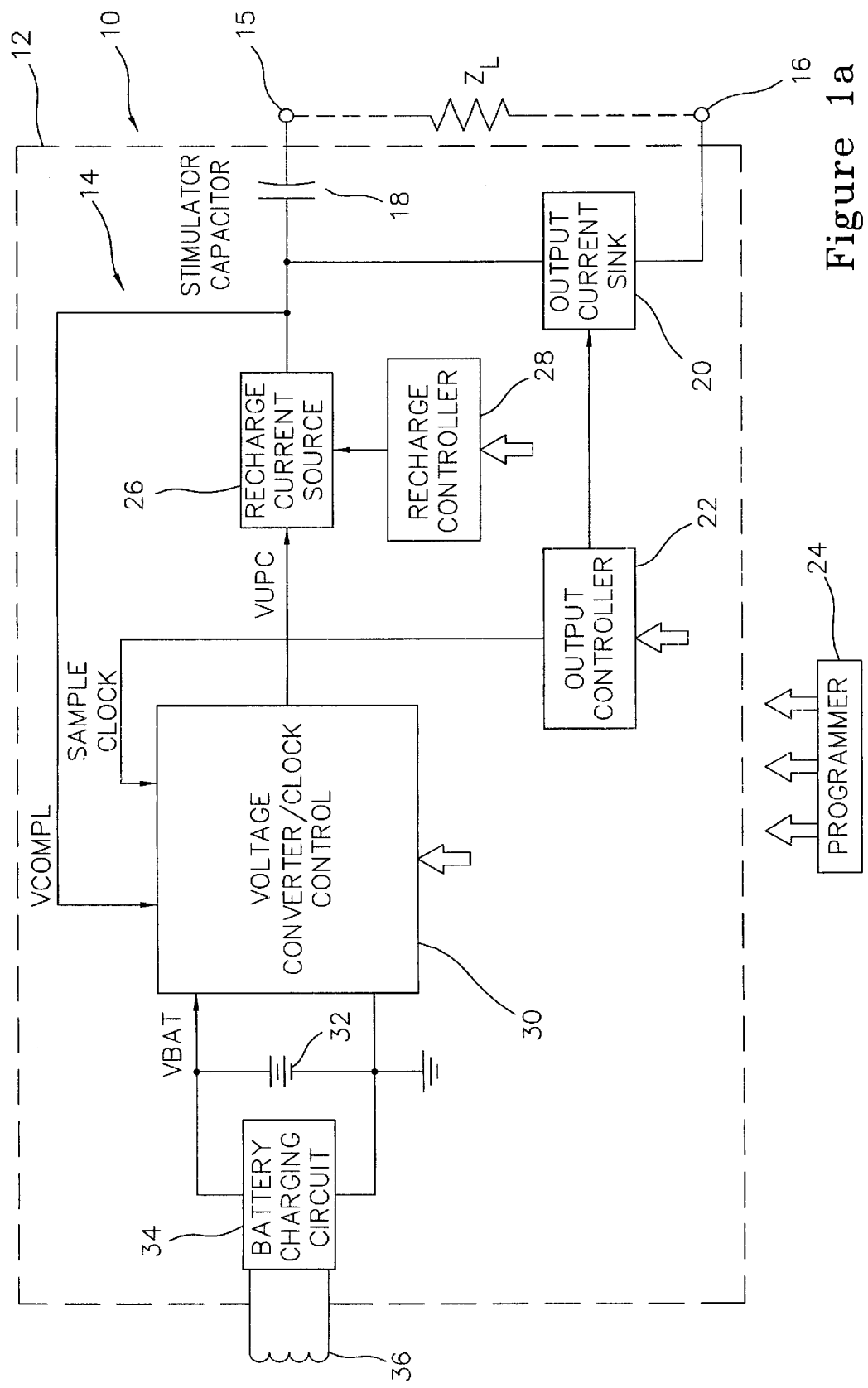
FIG. 1a shows a block diagram of voltage control circuitry in accordance with the present invention.

Attention is initially directed to FIG. 1a which is a block diagram of a preferred implantable device 10 including a housing 12. The housing contains electronic circuitry 14 for producing a current pulse between output electrodes 15,16 through a load impedance $Z_L$, e.g., body tissue. The electronic circuitry 14 includes an output (or "stimulator") capacitor 18 and an output current control device, e.g., current sink 20. The current sink 20 is controlled by an output controller 22. By activating current sink 20, capacitor 18 can discharge through sink 20 to produce an output current pulse through load impedance $Z_L$. The characteristics of the current pulse, e.g., amplitude, duration, repetition rate, are defined by controller 22 which is preferably programmable by an external programmer 24. The programmer 24 communicates with controller 22 via a communication channel, e.g., radio frequency (RF), not shown.

A recharge current control device, e.g., current source 26, is also connected to capacitor 18 to selectively apply a charging current to the capacitor. Current source 26 is controlled by recharge controller 28. Controller 28 is preferably programmable by external programmer 24 to control, for example, the on/off timing of current source 26. When source 26 is on and sink 20 is off, a current is applied to capacitor 18 to charge the capacitor toward voltage VUPC.

The voltage VUPC is produced in accordance with the present invention by a voltage converter/clock control circuit 30. The circuit 30 produces the voltage VUPC as a function of an applied battery voltage VBAT supplied by battery 32. Battery 32 is preferably rechargeable via a charging circuit 34. Energy is preferably supplied to the charging circuit 34 via coil 36 from an external source (not shown) generating an alternating magnetic field.

The circuit 30 is preferably programmable by external programmer 24. The circuit 30 functions to define a multiplication factor which relates VUPC to VBAT. That is, circuit 30 acts as an up/down voltage converter to multiply VBAT by a factor to produce VUPC. The factor can preferably be an integer or fraction and is determined based on the voltage value VCOMPL derived from capacitor 18.

Figure 1B:
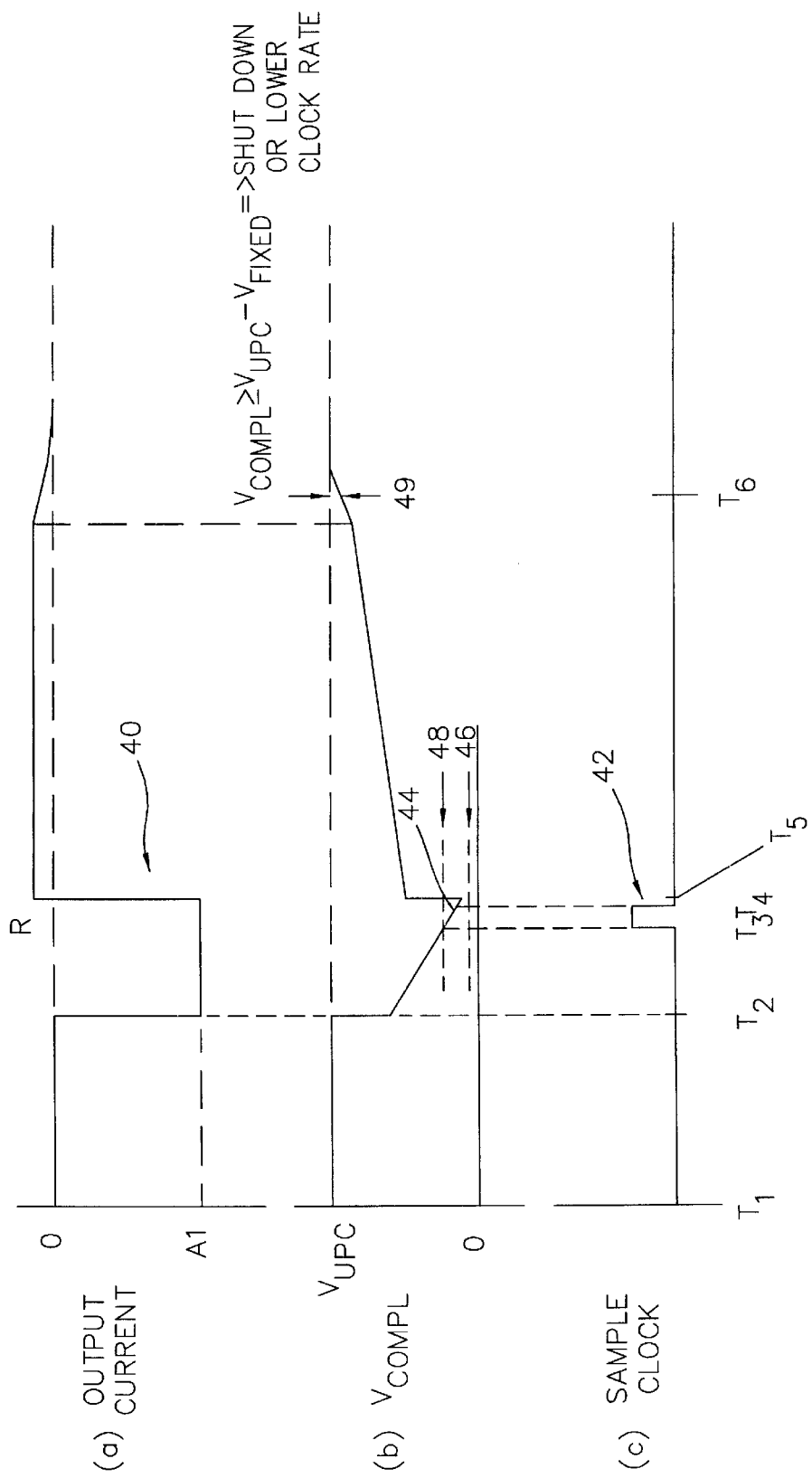
FIG. 1b shows an output current pulse produced by discharging an output capacitor, the output capacitor voltage, and a sample clock.

Attention is now directed to FIG. 1b which in line (a) represents an output current pulse 40 which is discharged by capacitor 18 through load $Z_L$. The wave form shows the current at a zero level between times t1 and t2. Line (b) represents the voltage VCOMPL at the positive terminal of capacitor 18 and is shown to be at level VUPC between times t1 and t2. Now assume that output current sink 20 turns on at time t2 to increase the output current pulse amplitude to A1 which is maintained to time t5, as dictated by controller 22 controlling output current sink 20.

FIG. 1b line (b) shows how the voltage VCOMPL varies between times t2 and t5 as capacitor 18 discharges through load $Z_L$. Between times t3 and t4, controller 22 generates a sample clock 42 to measure VCOMPL to determine the value of its final "droop" 44, i.e., the value reached by VCOMPL proximate to the end of the output current pulse at time t5. This measured value of VCOMPL at the sample clock is used by the voltage converter/clock control circuit 30 of FIG. 1a to select a multiplication factor to produce VUPC from VBAT.

Note that line (b) of FIG. 1b represents a low threshold 46 ($\Delta V_{LOWER}$) and a high threshold 48 ($\Delta V_{HIGHER}$) against which the droop value 44 will be compared to determine whether the multiplication factor, defined by circuit 30, should be adjusted. Also note that line (b) of FIG. 1b represents a difference 49 between the target charging voltage VUPC and the value of VCOMPL at t6 after the capacitor 18 has been recharged via current source 26. As will be discussed hereinafter, the magnitude of the difference 49 is used to control a clock rate which determines the rate at which the multiplication factor can be adjusted.

Figure 1C:
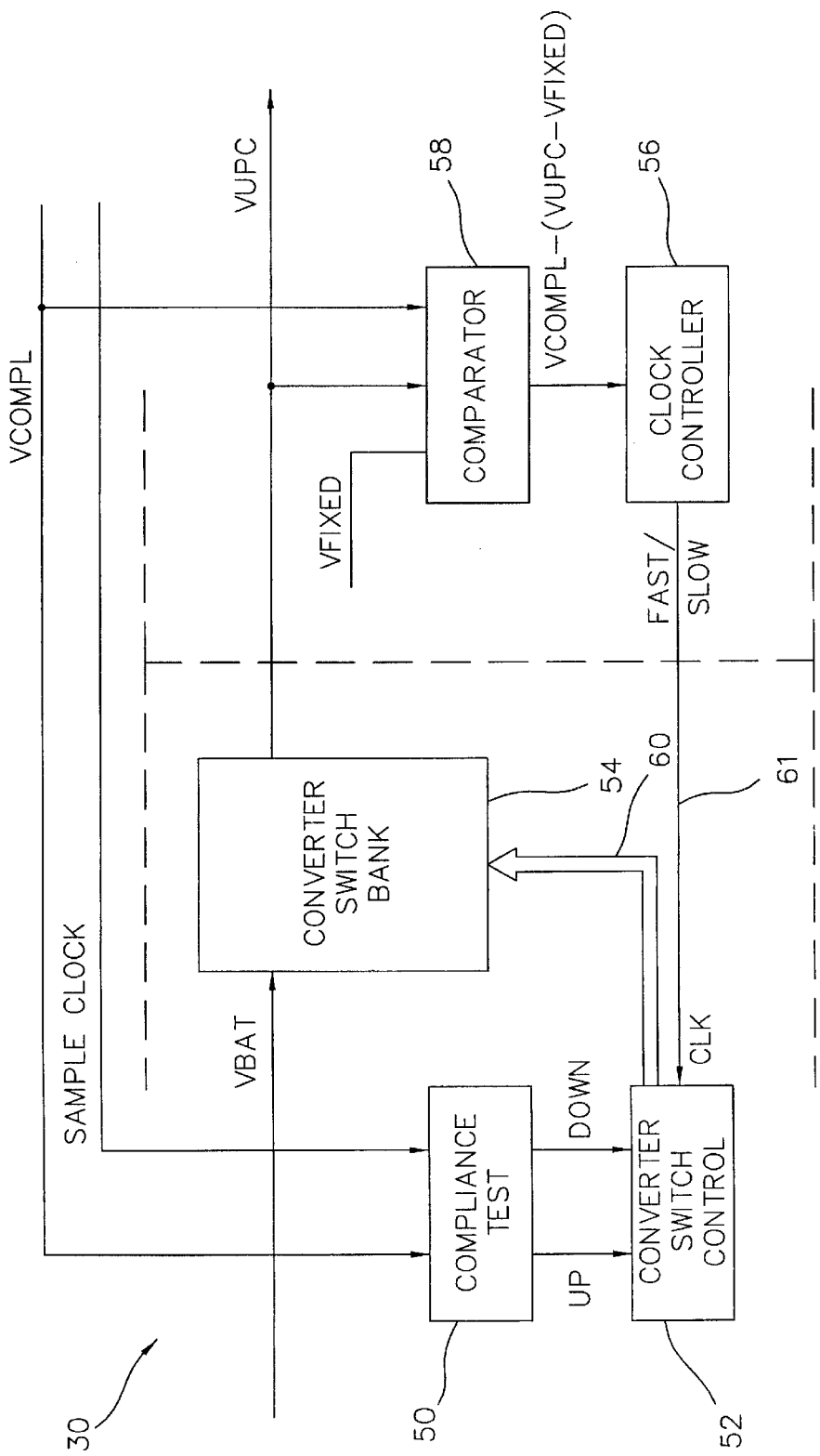

Attention is now directed to FIG. 1c which shows a block diagram of the voltage converter/clock control circuit 30 of FIG. 1a. The circuit 30 includes a compliance test circuit 50, a converter switch control circuit 52, a converter switch bank 54, a clock controller circuit 56 and a comparator 58. The circuits 50, 52 and 54 function to convert the voltage VBAT to produce the charging voltage VUPC. Briefly, the compliance test circuit 50 examines the relationship between the capacitor droop voltage 44 (i.e., VCOMPL at the sample clock) and the aforementioned thresholds 46, 48 to determine whether multiplication factor should be increased or decreased. The switch control circuit 52 then generates a command, supplied to switch bank 54 via lines 60, to operate individual switches in bank 54 to implement the desired multiplication factor.

The circuits 56, 58 function to respond to the difference value 49 (FIG. 1b line (b)) to establish an optimum clock rate for switch control circuit 52. That is, although it is desirable to reduce the difference value 49 to zero, excessive adjustment of the multiplication factor is wasteful of limited energy resources available from battery 32. The clock controller 56 functions to produce a clock rate on line 61 which is optimized to conserve energy and yet maintain the charged voltage on capacitor 18 at close to VUPC.

Figure 1D:
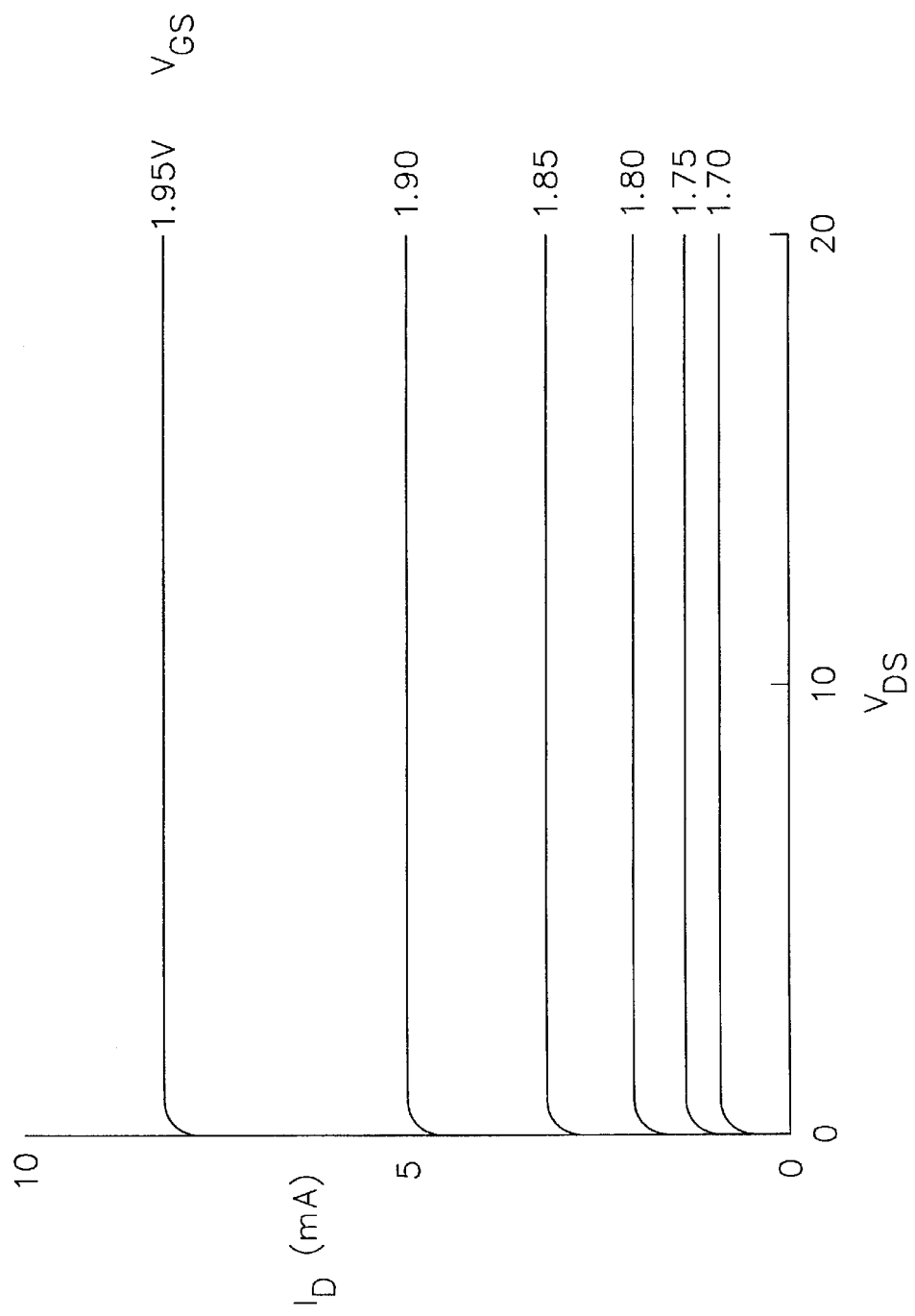
FIG. 1d shows the diagram illustrating field effect transistor (FET) drain current ($I_D$) versus drain-source voltages ($V_{DS}$), for different gate source voltages ($V_{GS}$)

It is pointed out that the output current sink 20 and recharge current source 26 of FIG. 1a are preferably fast acting, low loss circuits. In a preferred embodiment of the invention, these circuits are implemented as field effect transistors (FET). FIG. 1d depicts the constant current characteristic of a typical FET wherein the drain current ID is essentially flat over a wide drain-source voltage ($V_{DS}$) range. The drain current amplitude is primarily a function of the gate-source voltage $V_{GS}$. In FIG. 1a, the voltage $V_{GS}$ for current sink 20 is controlled by controller 22 and the voltage $V_{GS}$ for current source 26 is controlled by controller 28.

Figure 2A:
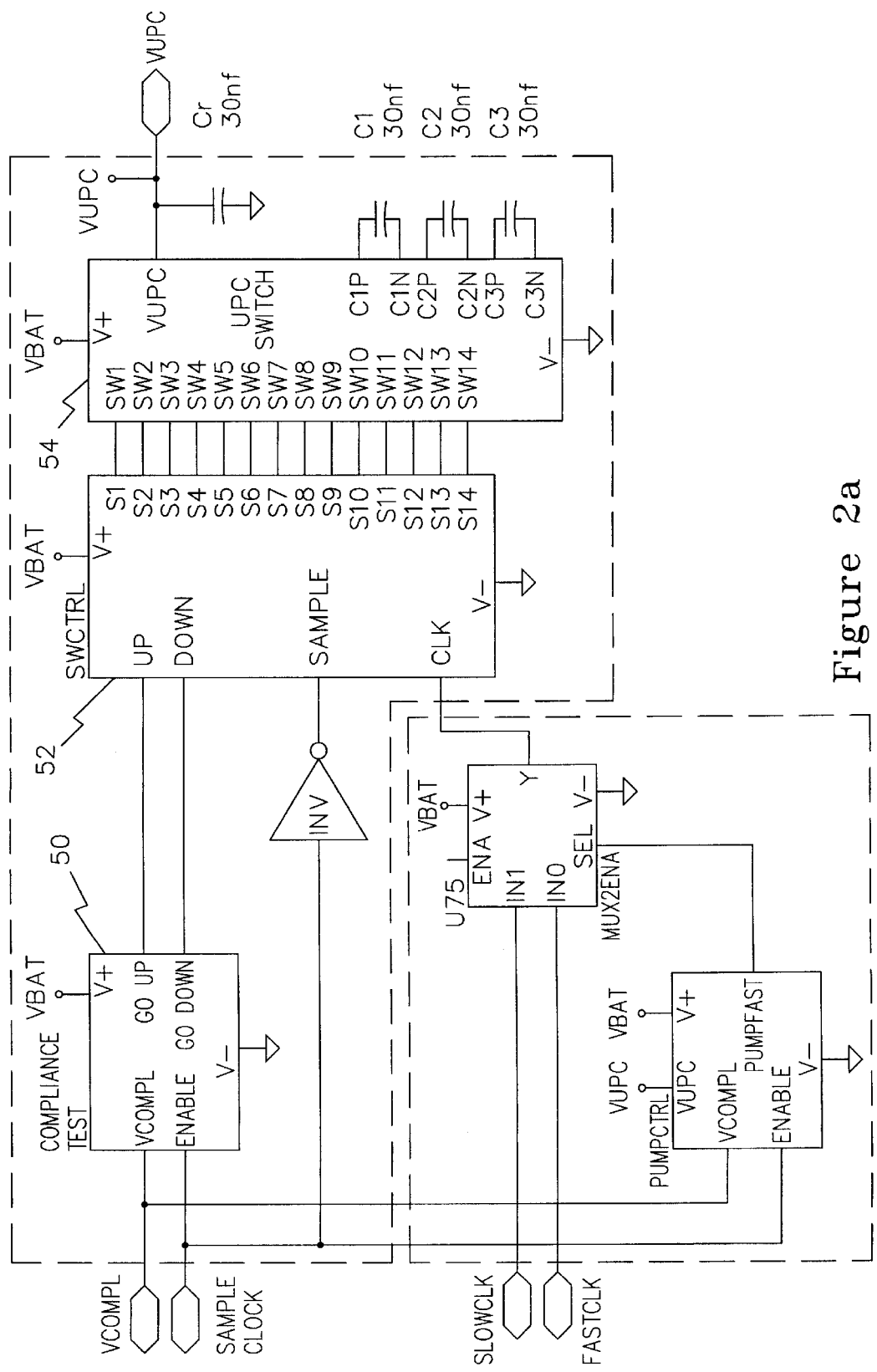
FIG. 2a indicates the automatic compliance voltage adjustment circuitry in block diagram form.

Attention is now directed to FIG. 2a which depicts an exemplary implementation of the conversion portion of FIG.

1c comprising the compliance test circuit 50, the switch control circuit 52 and the converter switch bank 54. The switch bank can use a well-known method for up-conversion by placing capacitors in parallel across a voltage source for charging so that each capacitor is charged to that voltage. Then the capacitors are placed in a series configuration (by switching means) such that the overall voltage is the sum of the voltages on the individual capacitors. A similar method, old in the art, of placing, say, two same value capacitors in series and charging the group in parallel with the voltage source, will give one half of the voltage source voltage when those two same value capacitors are used in parallel without the battery. Bank 54 is depicted in FIG. 2a as having multiple switch inputs SW1–SW14 for controlling multiple FET switches internal to bank 54. These internal switches control multiple capacitors, e.g., C1–C3, to achieve the desired multiplication factor.

Figure 2B:
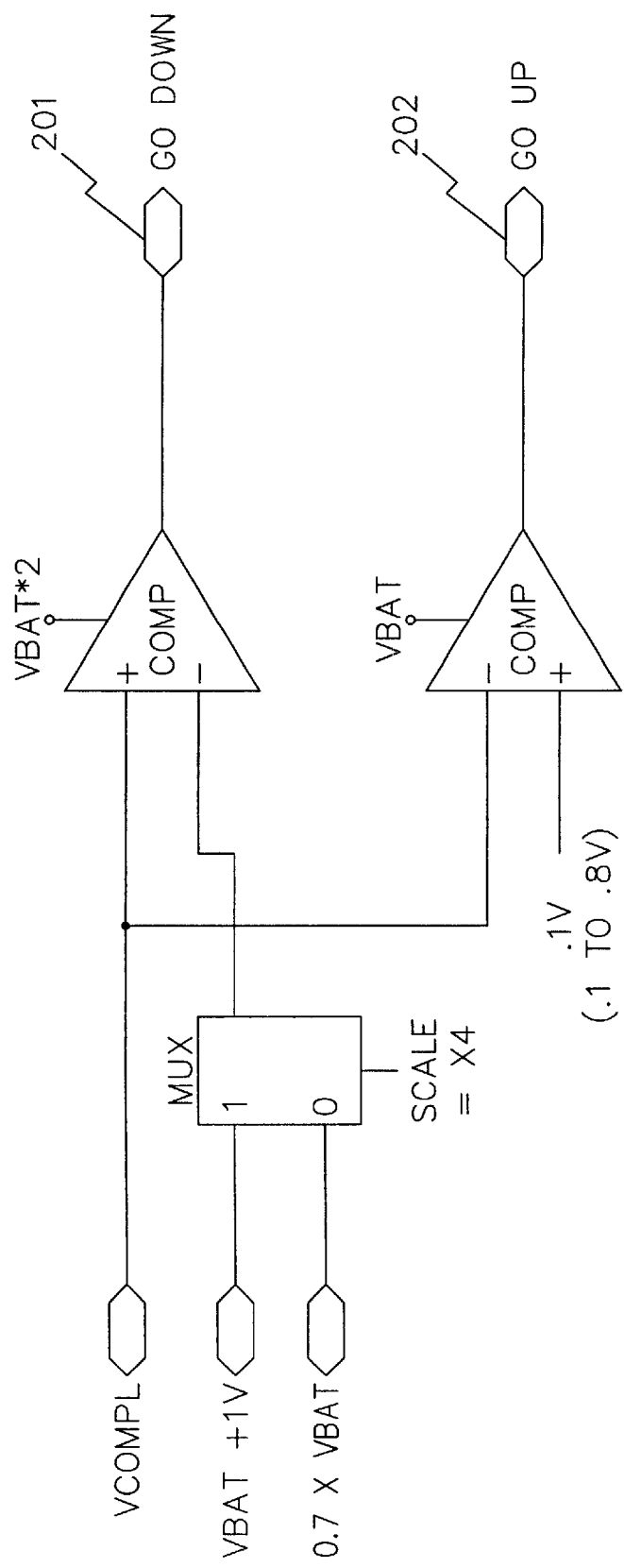
FIG. 2b shows the compliance test in block diagram form.
Figure 2C:
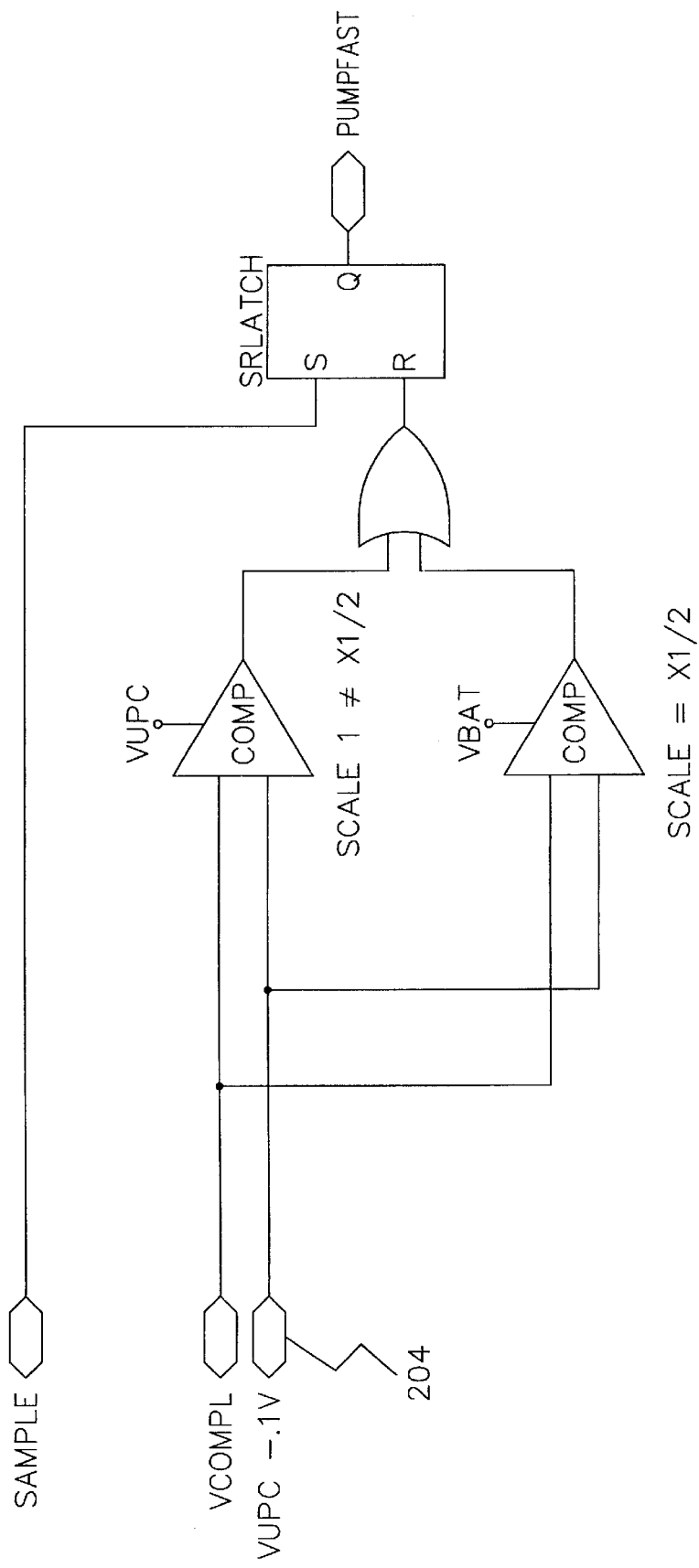
FIG. 2c indicates the pump clocking control in block diagram form.

The compliance test block diagram is shown in FIG. 2b, while FIG. 2c illustrates the pump control block diagram. The goal of the compliance test block is to determine when the compliance voltage VCOMPL is too high or too low. The switch control circuit clocking controls the switching rate of the FET switch bank 54. The switching rate is reduced to the extent possible to reduce power consumption. In FIG. 2b, the compliance voltage VCOMPL is compared to either [VBAT+1] volt or [0.7 VBAT] volt, and the GO DOWN 201 or GO UP 202 decision outputs direct the switch control block (52) to take action.

Figure 3A:
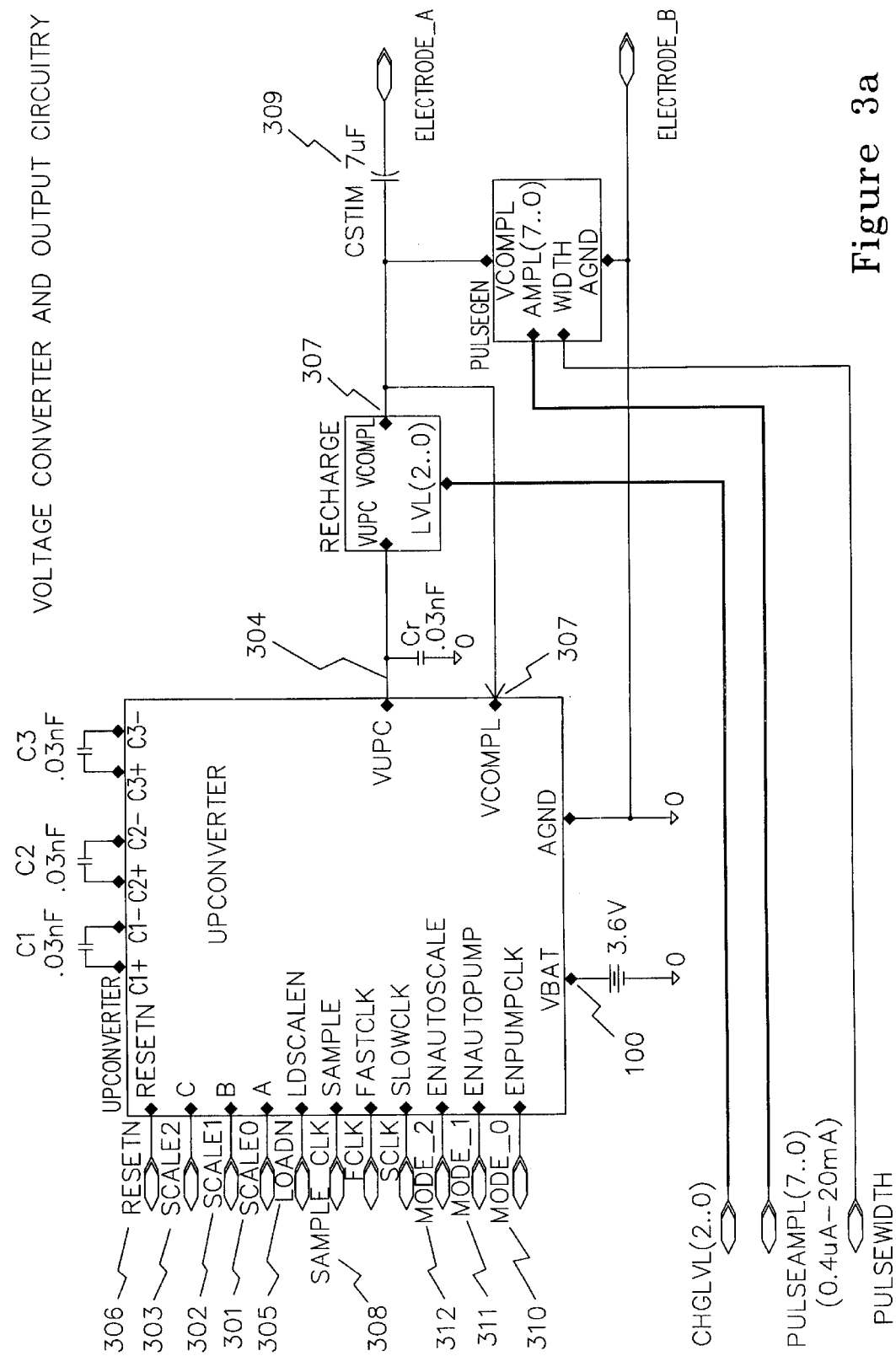
FIG. 3a shows the voltage converter and output circuitry.

This upconverter takes the battery voltage VBAT (FIG. 3a, 100) and multiplies it by a programmed scale factor, set by lines SCALE_0 (301), SCALE_1 (302), and SCALE_2 (303), to generate the voltage, VUPC (304), necessary for a pulse generation circuitry. The multiplication factors in the version of the up/down converter shown are ½×, 1×, 1½×, 2×, 2½×, 3×, and 4×. A different set or an expanded set of multiplication factors can be implemented with more capacitors and switches, as desired.

The control bits are loaded into an up/down counter using the LOADN (305) line. A low on the reset line, RESETN (306), places the converter in the 1× scale factor setting.

The upconverter can be placed in automatic adjustment mode so that the scale factor moves to the optimal value based on sampling of the compliance voltage, VCOMPL (307), measured at the end of the stimulation pulse.

The time at which to sample the compliance voltage is controlled with the SAMPLE_CLK (308) line. At that time, the automatic adjustment of the battery voltage multiplier circuit is based on the amount of "unused" compliance voltage left at the end of the stimulation pulse. If the "unused" compliance voltage is below a hardwired threshold, Vlower, where Vlower is typically the range 0.1 V to 0.8 V, then this indicates, or is defined as the case that, there was insufficient voltage to adequately drive the desired pulse amplitude. The multiplier factor will increase to the next higher multiple.

If the "unused" compliance voltage is above an upper hardwired threshold, Vhigher, this indicates that there is excess compliance voltage, and the factor will decrease to the next lower multiple as a power-saving feature.

Vhigher is set to either [0.7 VBAT] or [VBAT+1 v] depending on the currently set scale factor.

Voltage conversion is achieved by switching among the input voltage and up to three capacitors, and depositing charge on a fourth, or reservoir, capacitor. Clocking within the switched-capacitor section occurs at a normal frequency of 20 kHz.

When sufficient charge to reach the target voltage has been deposited on the stimulation capacitor, CSTIM (309), the clock can be automatically set to a lower rate (which could be 0 Hz) to save power. This shutdown point is determined by monitoring the compliance voltage, VCOMPL (307), and comparing it to the upconverter output voltage minus a hardwired threshold [VUPC–0.1V] (FIG. 2c, 204). The automatic scaling and clock shutdown modes are set with the MODE_0 (310), MODE_1 (311) or MODE_2 (312) lines.

Power can be saved by automatically decreasing upconverter clock rate to a lower frequency. The switching of the FET switches in the switch bank 54 consumes power proportional to the rate of switching. The automatic adjustment of the voltage converter clock rate is based on the state of charge of the stimulation capacitor 18. After a stimulation pulse has drained charge from the stimulation capacitor, recharge current is supplied to it and the voltage on it will rise toward the upconverter voltage. As the voltage on the stimulation reservoir capacitor nears the voltage VUPC, it passes a threshold, which triggers the switching of the upconverter rate to a lower frequency, which includes a frequency of 0 Hz.

A control signal is generated and used to lower the multiplier factor of the upconverter. A comparator is used to compare a reference voltage with the compliance voltage at a particular sample time, viz., the end of the stimulation pulse. As another power saving feature, the reference voltage and the comparator are only powered during this sample time interval. A capacitor normally in parallel with the battery is stacked on top of the battery during the sampling interval. This is a voltage doubler.

This voltage is used to power the comparator and is also used to turn on a diode-connected FET that feeds into the positive side of the battery. The FET-diode circuit part provides a voltage drop across the diode, due to the small but finite conducting resistance of the diode. This one diode voltage drop provides a comparator reference voltage that is used to decide when to change from the 4× to the 3× multiplication factor.

The upconverter multiplier factor step size can be either ½ the battery voltage or one times the battery voltage in the following sequence: ½×, 1×, 1½×, 2×, 2½×, 3×, and 4×. When the step size should be ½ the battery voltage, a different reference voltage is applied to the comparator. This reference voltage is developed utilizing capacitance values for the capacitors, which are chosen in definite ratios to each other. One capacitor is initially connected in parallel with the battery while the other is shorted. Then during the sampling time the two capacitors are connected in parallel and a resultant voltage is developed. For example, for two capacitor which have a parallel capacitance total of 10 units, the first capacitor has a capacitance of 7 units and the second capacitor has a capacitance of 3 units. Thus for the first capacitor ratio of 7:10 and the second capacitor ratio of 3:10, the resultant voltage developed is 0.7 VBAT.

Figure 3B:
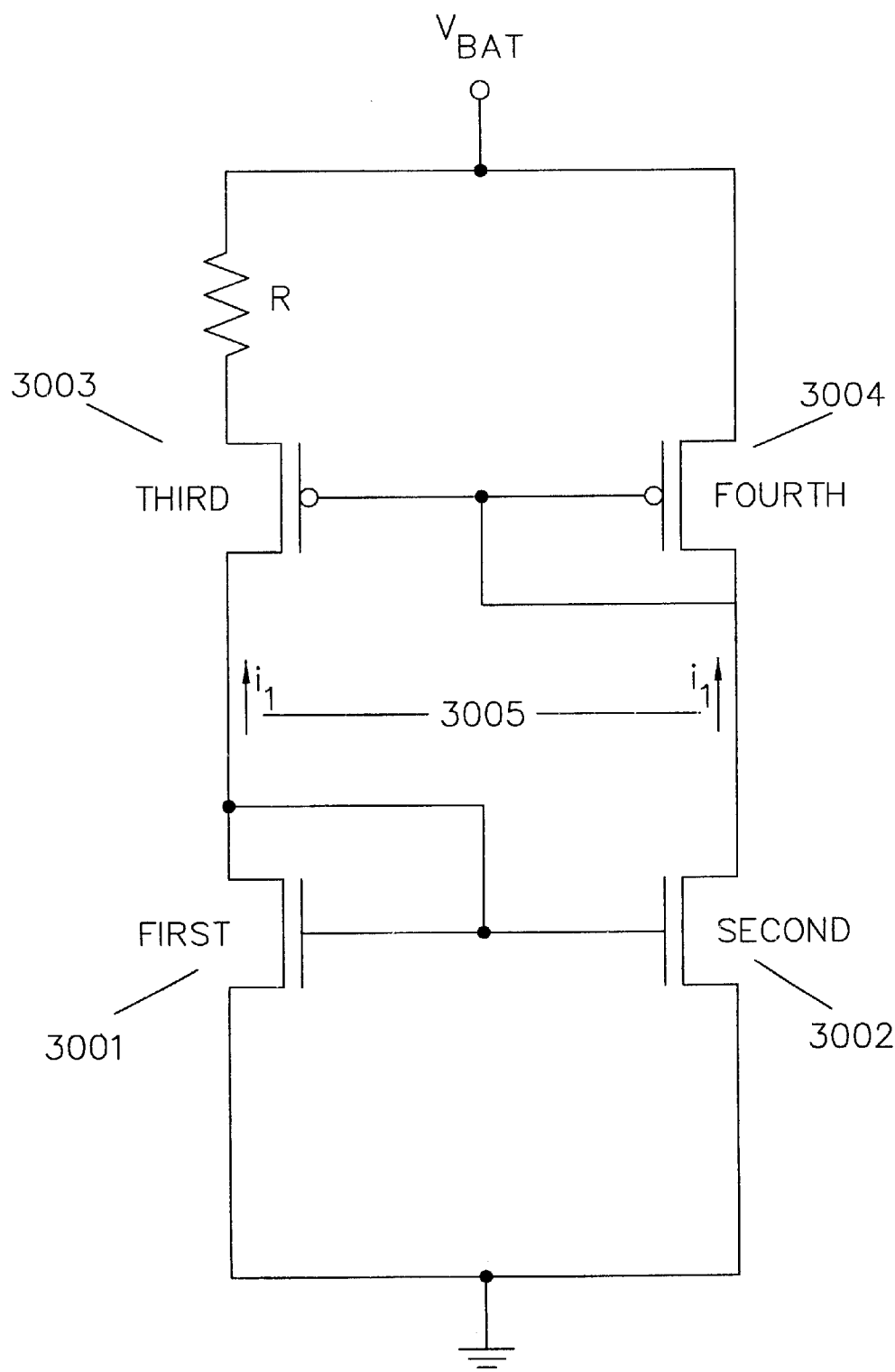
FIG. 3b shows the current mirror-based circuit for producing a sub-threshold reference voltage.

Another aspect of this invention uses a cross-coupled current mirror (FIG. 3b, 3001, 3002) configuration to generate the threshold voltage, Vchargeth. A current mirror is used to generate a known, low value current (3005) that is run through two FETs (3003, 3004) operating in a sub-threshold condition. When operating in a sub-threshold condition, the drain current of an FET is exponentially related to the gate-to-source voltage, Vgs, such that for each approximately 100 mV of change in Vgs, the drain current will change by a factor of 10. If the size of two FETs (3003, 3004) (which have their gates tied together and which are forced to have the same drain current by said current mirror) are chosen of values which are in the ratio of 10:1, then the FET that is 10 times larger will have a current density which is lower by a factor of 10. This results in Vgs of the larger FET being 100 mV different from the smaller FET. This 100 mV potential is used as a reference voltage, with respect to the up/down voltage, into the comparator monitoring the state of charge of the stimulation capacitor.

Another aspect of this present embodiment is to produce a sub-threshold reference voltage, Vlowth, in the range 0.1 V to 0.8 V, using a similar current mirror method, as above, but developing a set voltage above ground voltage. This sub-threshold current is used to determine when the compliance voltage during the sample time is too low, so that the upconverter will move to the next higher multiplication scale factor.

In order to carry out switching control, the converter is set to a particular scale factor; a value is loaded into a 3-bit up/down counter. The output of this counter goes into a logic block that decodes this setting and enables or disables appropriate switches necessary to effect this scale setting. The clock then dynamically controls the actual turning on and off of these switching capacitors ("State 0"), and, second, the switch settings that deposit the charge onto the output reservoir capacitor ("State 1"). A two-phase clock is used with a separation between the phases so that there is an off time between states 0 and 1. This off time ensures that transient switching paths will not drain any of the charge off the switching capacitors, between state changes.

Figure 4:
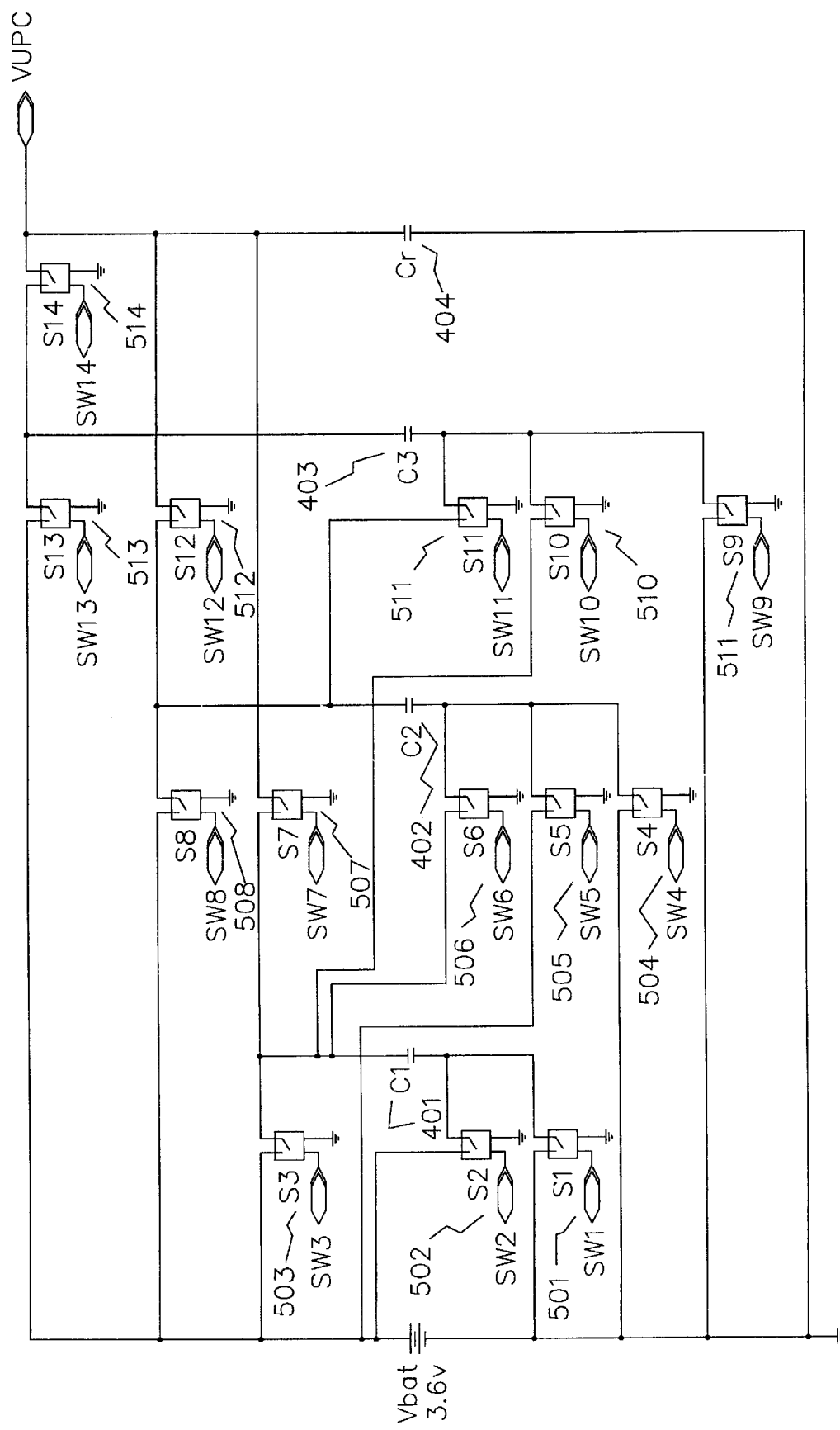
FIG. 4 depicts the ideal switch model for the up/down converter.
Figure 5A:
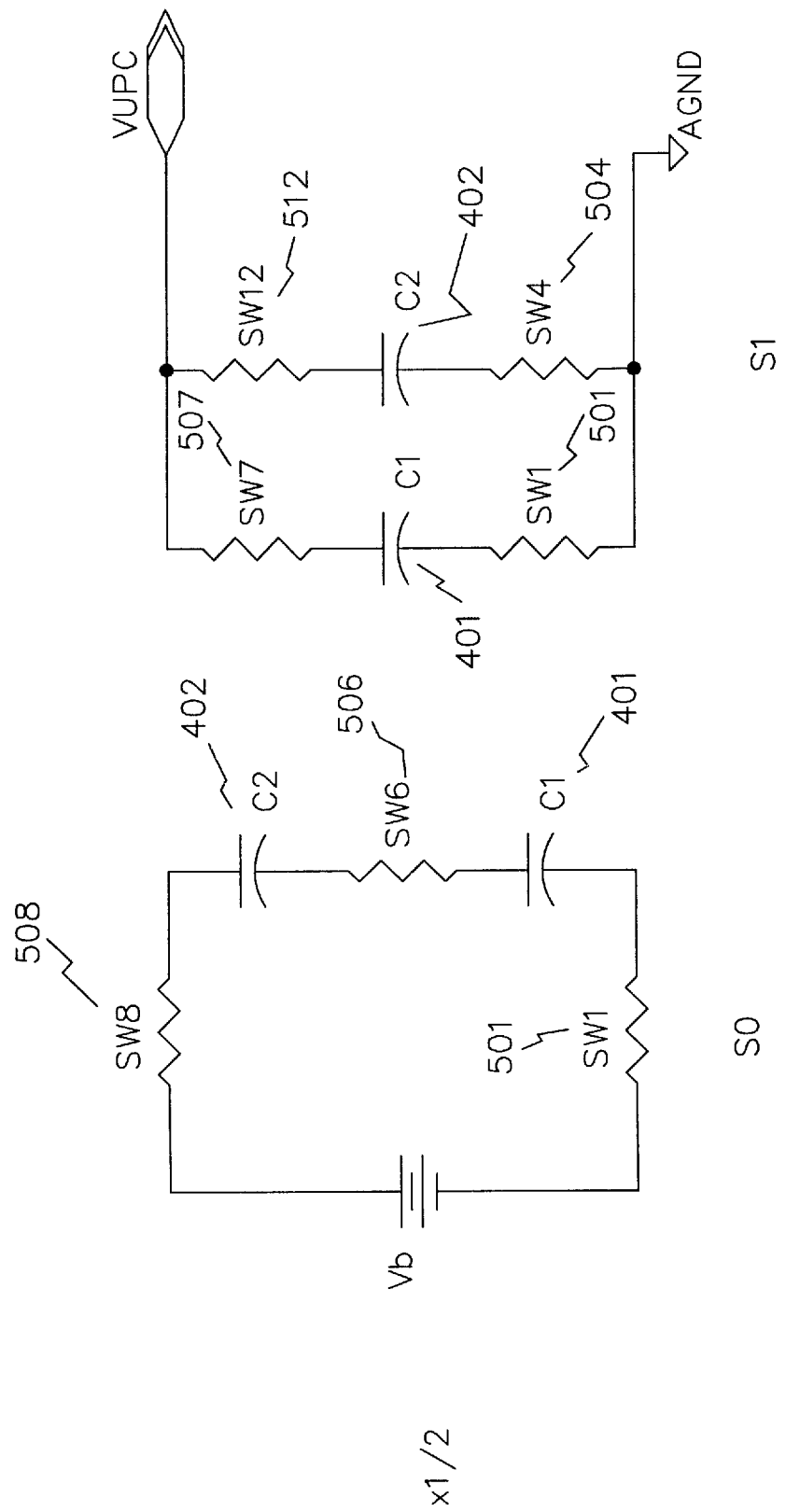
FIG. 5a shows the switch and capacitor settings in a charging configuration (S0) and in a discharging configuration (S1) for a multiplying factor of ½, i.e., a down-conversion mode.

FIG. 4 depicts the up/down converter ideal switch model. The capacitors to be electronically arranged are shown: C1 (401), C2 (402), C3 (403) and the reservoir capacitor Cr (404). FIG. 5 shows the states of the up/down-converter with respect to the initial and final states of the capacitors, to operate the up/down-converter in the different multiplication factor modes. Resistors represent the switches. FIG. 5a shows the switch and capacitor settings in a charging configuration (S0) and in a discharging configuration (S1) for a multiplying factor of ½, that is a down-conversion mode. Capacitors C1 (401) and C2 (402) are used as well as switches (that are conducting) SW1 (501), SW6 (506), and SW8 (508) in the charging mode. In the discharging mode capacitors C1 (401) and C2 (402) are used together with switches SW1 (501), SW4 (504), SW7 (507) and SW12 (512).

Figure 5B:
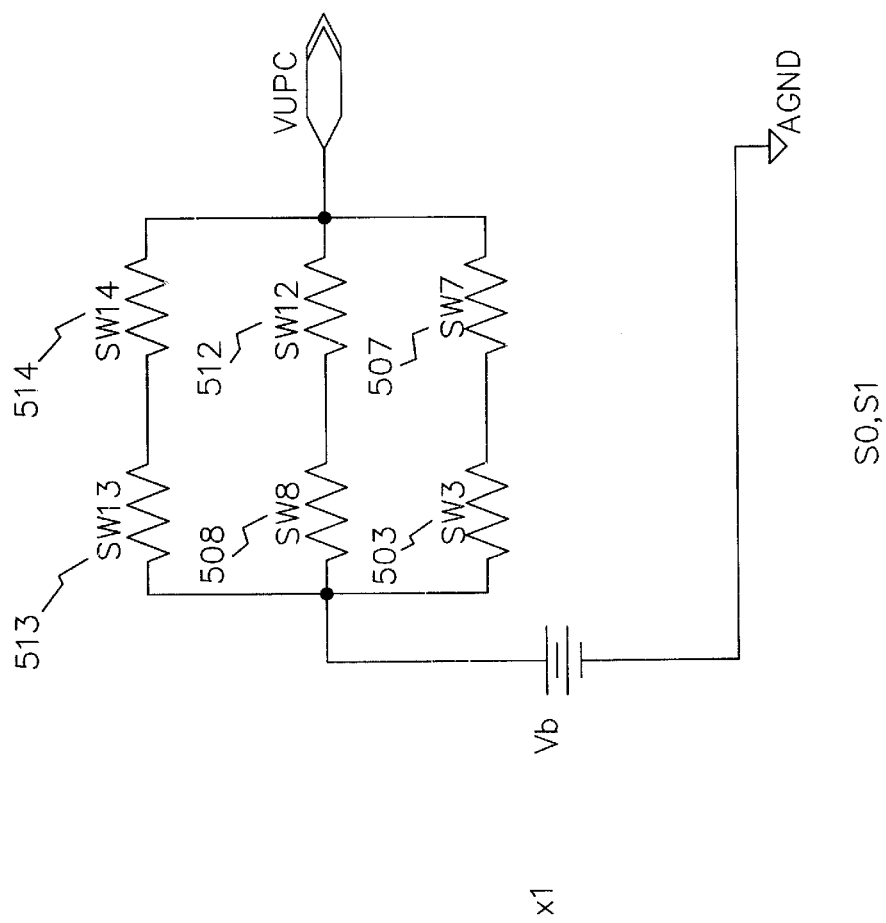
FIG. 5b has an analogous depiction for a multiplication factor of 1.
Figure 5C:
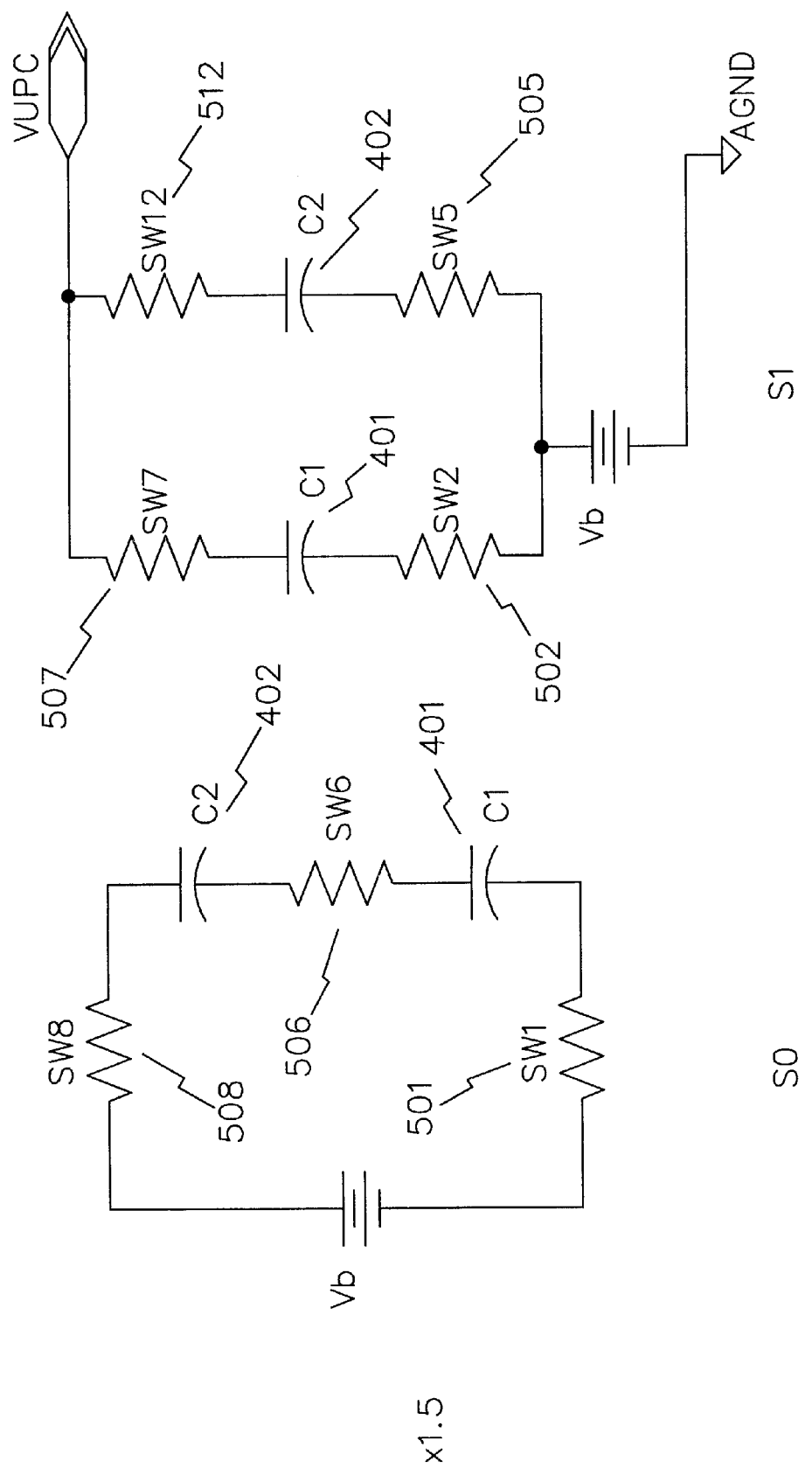
FIG. 5c pictures an analogous situation for a multiplication factor of 1.5.
Figure 5D:
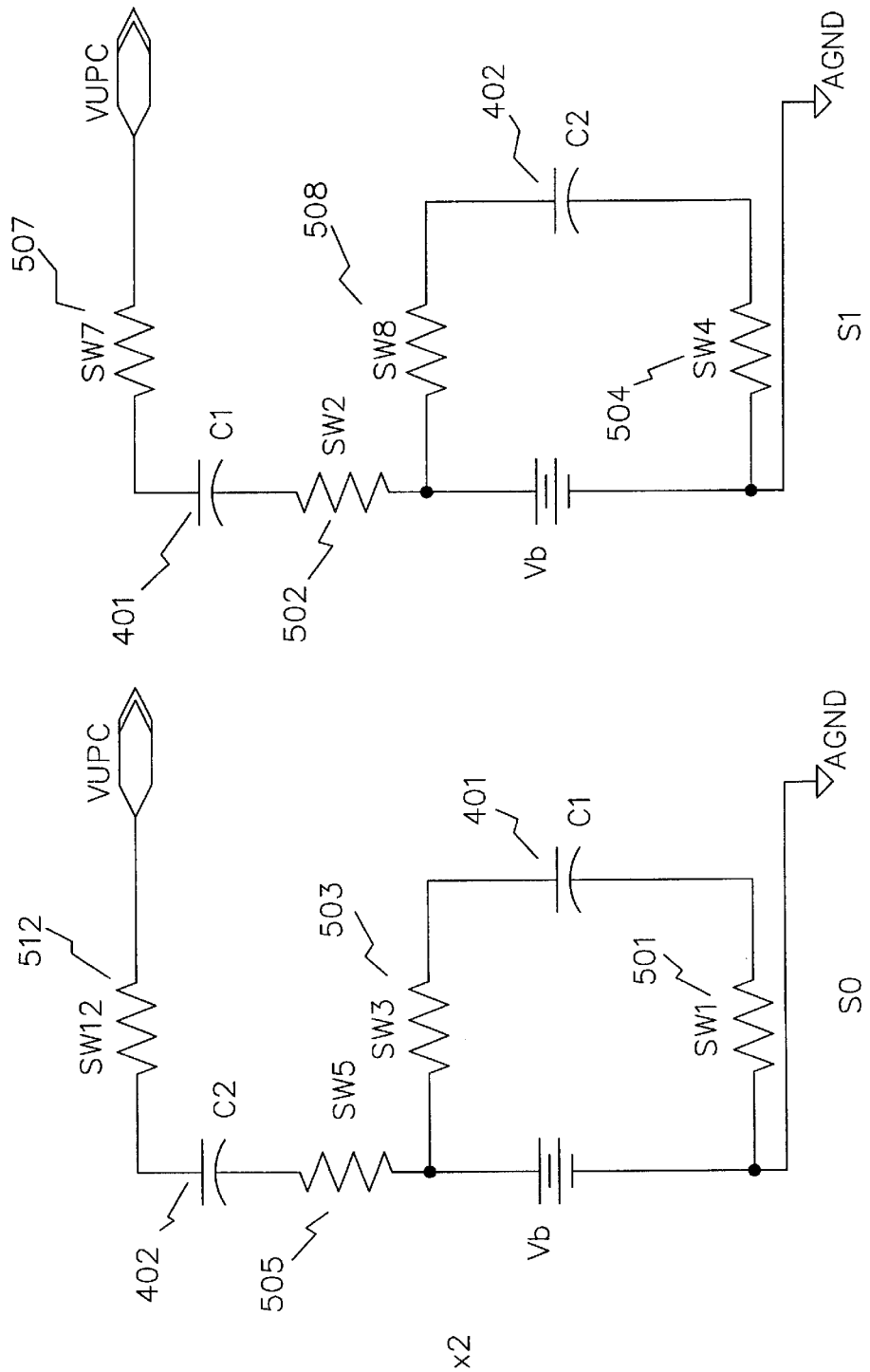
FIG. 5d shows an arrangement for the multiplication factor of 2.

FIG. 5b has an analogous depiction for a multiplication factor of 1 utilizing only switches (that are conducting) SW3 (503), SW7 (507), SW8 (508), SW12 (512), SW13 (513), and SW14 (514). FIG. 5c pictures an analogous situation for a multiplication factor of 1.5. Capacitors C1 (401) and C2 (402) are charged and discharged. Switches (that are conducting) SW1 (501), SW6 (506) and SW8 (508) are used in the charging state (S0); switches SW2 (502), SW5 (505), SW7 (507), SW12 (512) are utilized in the discharging mode. FIG. 5d shows the multiplication factor 2 arrangements. Again capacitors C1 (401) and C2 (402) are charged and discharged. Charging makes use of switches (that are conducting) SW1 (501), SW3 (503), SW5 (505) and SW12 (512). Discharging utilizes SW2 (502), SW4 (504), SW7 (507), and SW8 (508).

Figure 5E:
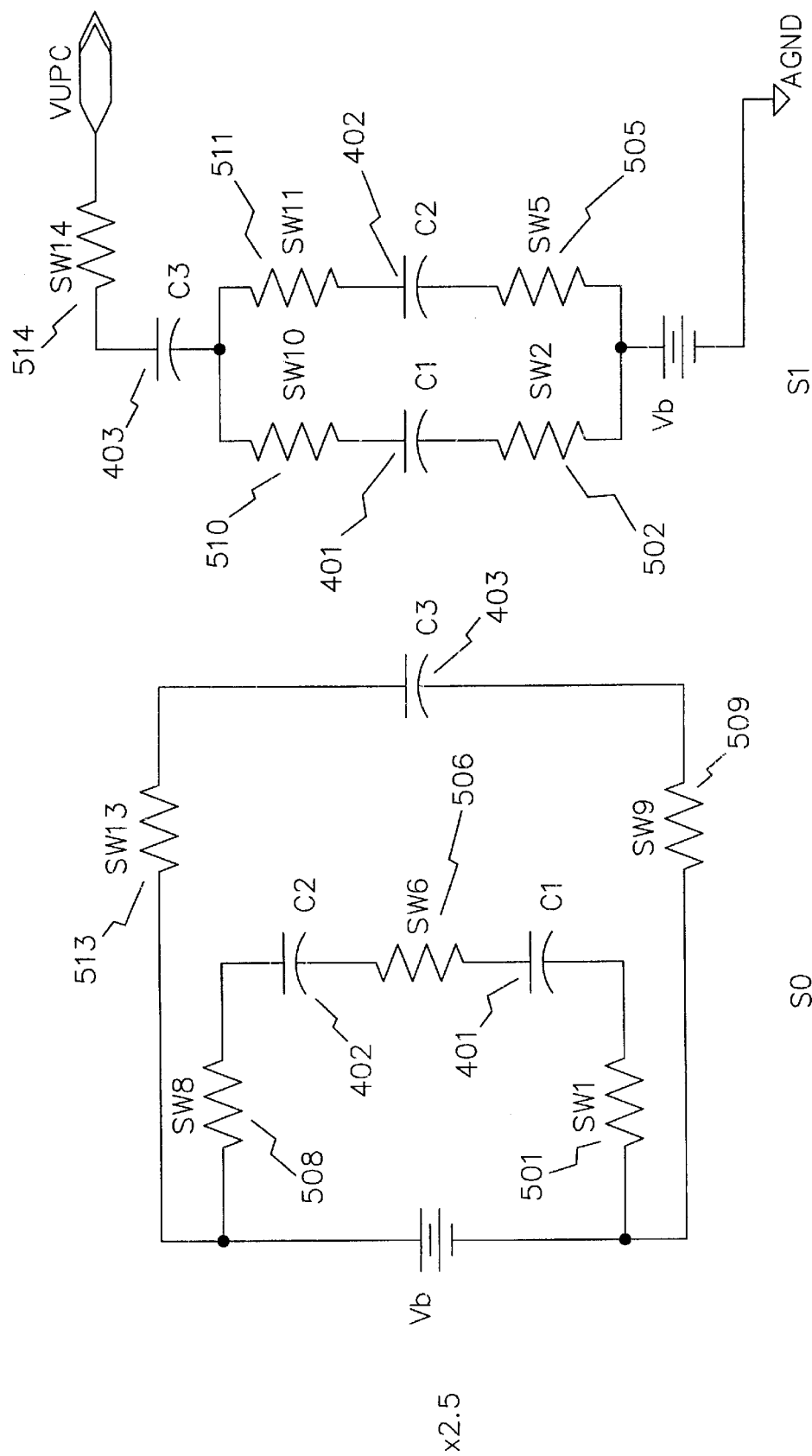
FIG. 5e presents the switch and capacitor combinations for the multiplication factor of 2.5.
Figure 5F:
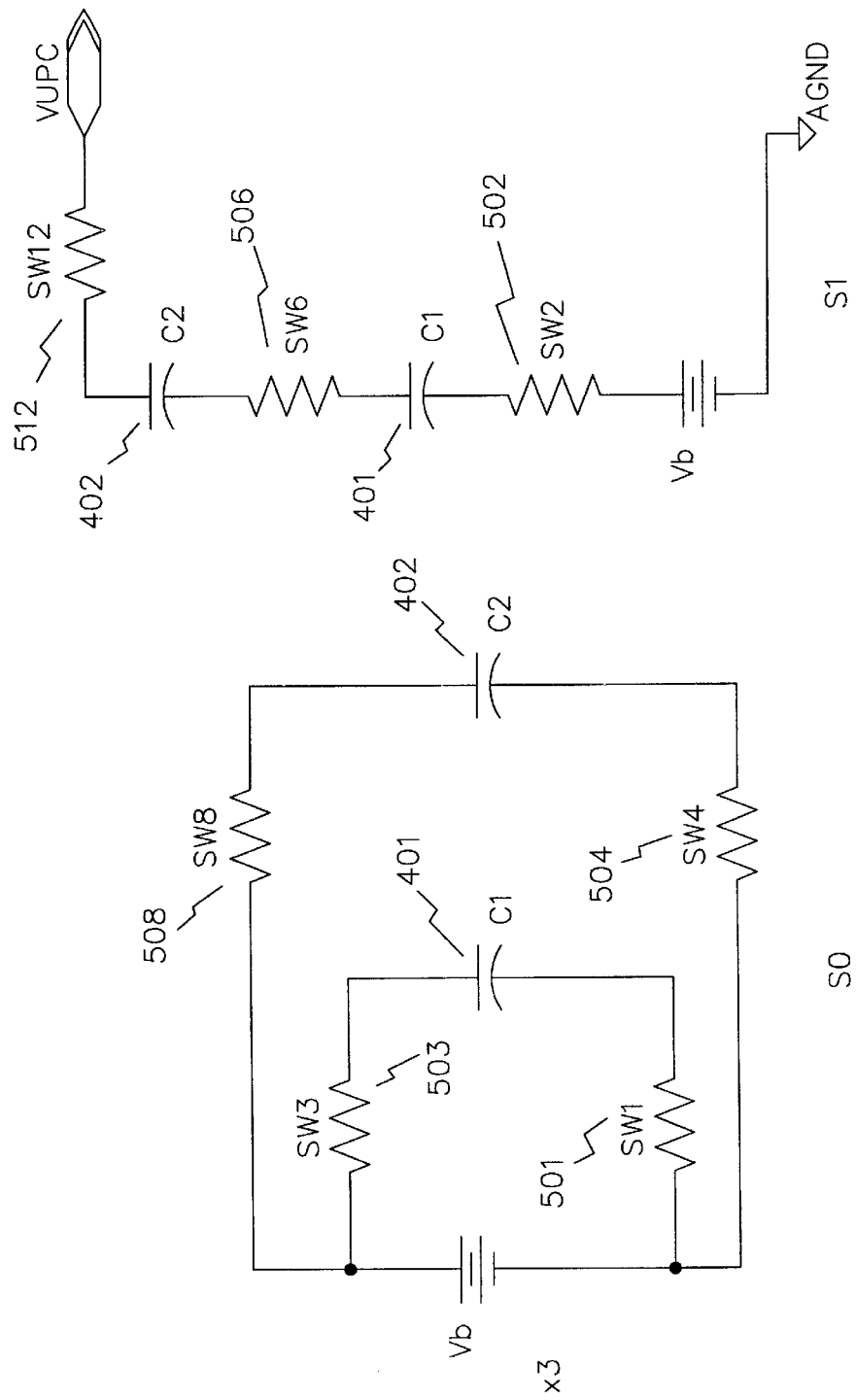
FIG. 5f shows the similar situation for the multiplication factor 3.
Figure 5G:
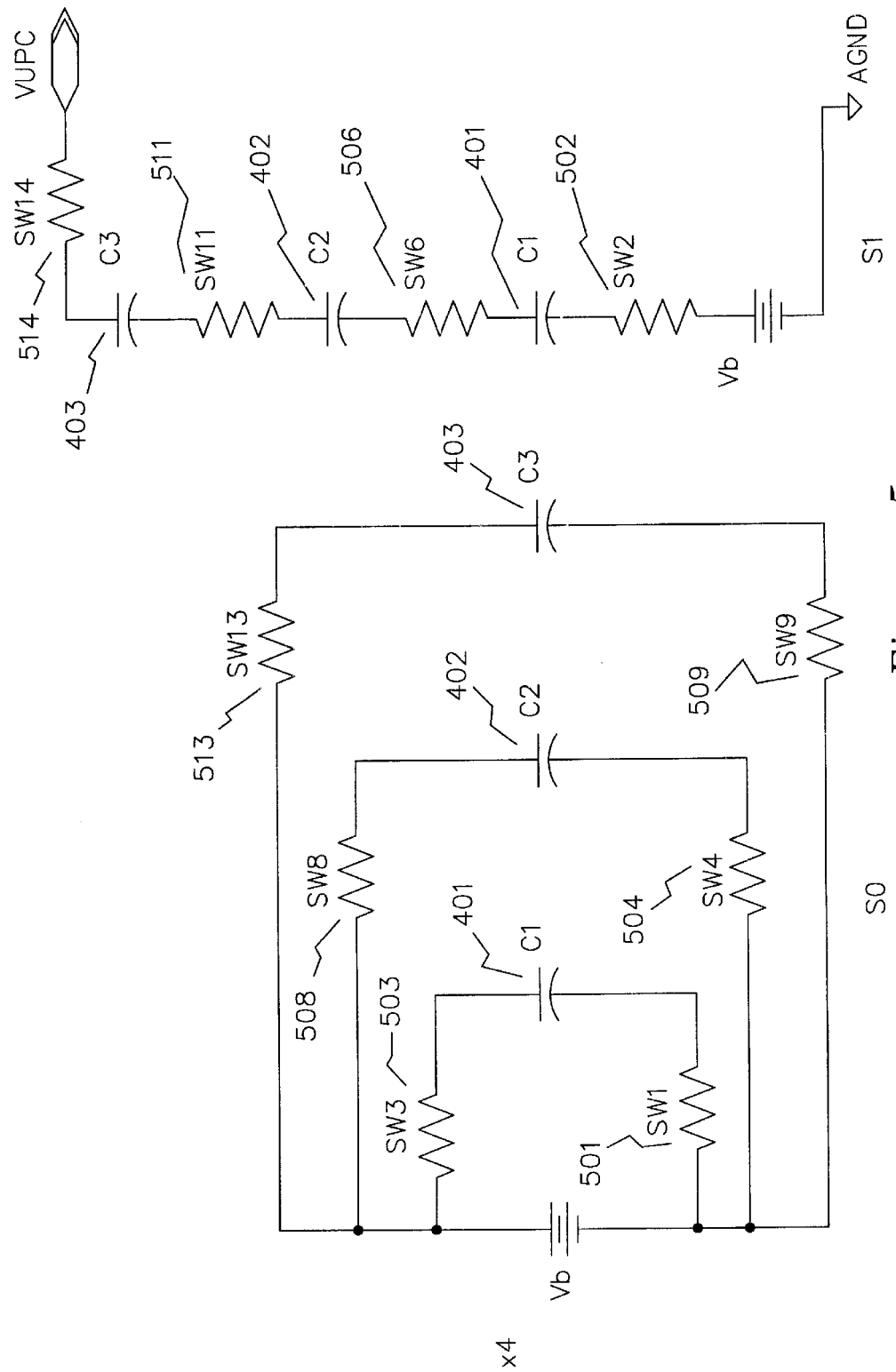
FIG. 5g is an analogous presentation for the multiplication factor 4.

FIG. 5e presents the switch and capacitor combinations for the multiplication factor 2.5. Here the three capacitors are charged and discharged, C1 (401), C2 (402) and C3 (403). In the charging state, S1, the conducting switches are SW1 (501), SW6 (506), SW8 (508), SW9 (509) and SW13 (513). In the discharge state, S1, the conducting switches are SW2 (502), SW5 (505), SW10 (510), SW11 (511) and SW14 (514). FIG. 5f shows the similar situation for the multiplication factor 3. C1 (401) and C2 (402) are the capacitors involved; conducting switches SW1 (501), SW3 (503) and SW4 (504) and SW8 (508) are on for the charging state; SW2 (502), SW6 (506) and SW12 (512) are on for the discharging state. FIG. 5g is an analogous presentation for the multiplication factor 4. Here, the three capacitors C1 (401), C2 (402) and C3 (403) are charged and discharged. In the charging state, S0, the conducting switches are SW1 (501), SW3 (503), SW4 (504), SW8 (508) and SW13 (513). In the discharging state, the conducting switches are SW2 (502), SW6 (506), SW11 (511), and SW14 (514).

In the automatic scale adjustment mode, the output compliance voltage is sampled and compared to high and low thresholds. If this comparison indicates that the voltage is too low, the up/down counter will count up and a different combination of switches will be enabled to effect a higher multiplication factor. If the comparison indicates the voltage is too high, the counter will count down and yet another combination of switches will be enabled that effect a lower multiplication factor.

The counter will only increment or decrement by one each time a sample of the compliance voltage is taken. When the counter reaches its minimum or maximum value, it will not further decrement or increment, respectively, even if the voltage sample indicates that a scale change is necessary.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for supplying a current pulse to a load impedance, said apparatus comprising;
   a stimulator capacitor;
   an output current control device for selectively discharging said stimulator capacitor to produce an output current pulse through said load impedance;
   a battery supplying a battery voltage;
   voltage converter circuitry for producing an output voltage signal to charge said stimulator capacitor; and wherein
   said voltage converter circuitry comprises:
      a plurality of converter capacitors;
      a plurality of switches configured for directing charge from said battery to said converter capacitors in a first mode of operation and configured for directing charge from said converter capacitors to said stimulator capacitor in a second mode of operation; wherein the selection of switches in said first and second modes of operations determines a voltage multiplication factor;
      clock circuitry for periodically switching said switches from said first to said second modes of operation; and
      measurement circuitry for periodically adjusting said voltage multiplication factor in response to a voltage measured across said stimulator capacitor.

2. The apparatus of claim 1 wherein said output current control device defines the duration of said output current pulse.

3. The apparatus of claim 2 wherein said voltage across said stimulator capacitor is measured proximate to the end of said output current pulse; and wherein said voltage multiplication factor is adjusted in response to said measured voltage.

4. The apparatus of claim 2 wherein said output current control device is programmable to define the duration and/or frequency of said output current pulse.

5. The apparatus of claim 1 wherein said clock circuitry is responsive to said measurement circuitry for determining the rate of adjustment of said multiplication factor.

6. The circuit apparatus of claim 1 further including a recharge current control device responsive to said output voltage for supplying a current to charge said stimulator capacitor.

7. The circuit apparatus of claim 6 further including a programmed controller for controlling said recharge current control device.

8. The circuit apparatus of claim 1 wherein said battery is rechargeable.

9. An apparatus suitable for supplying a current pulse to a load impedance, said apparatus comprising;
   a stimulator capacitor;
   a battery supplying a battery voltage;
   voltage converter circuitry for producing an output voltage signal to charge said stimulator capacitor; and wherein
   said voltage converter circuitry comprises:
   a plurality of converter capacitors;
   a plurality of switches configured for directing charge from said battery to said converter capacitors in a first mode of operation and configured for directing charge from said converter capacitors to said stimulator capacitor in a second mode of operation; wherein the selection of switches in said first and second modes of operations determines a voltage multiplication factor;
   clock circuitry for periodically switching said switches from said first to said second modes of operation at a clock rate; and
   measurement circuitry for periodically adjusting said voltage multiplication factor in response to a voltage measured across said stimulator capacitor.

10. The apparatus of claim 9 wherein said multiplication factor is increased when said voltage measured across said stimulator capacitor is below a threshold voltage.

11. The apparatus of claim 9 wherein said multiplication factor is decreased when said voltage measured across said stimulator capacitor is above a threshold voltage.

12. The apparatus of claim 9 wherein said clock rate is adjustable according to said voltage measured across said stimulator capacitor.

13. A method for generating a voltage across a stimulator capacitor suitable for supplying a current pulse to a load impedance, said method comprising the steps of:
   periodically supplying charge from a voltage source to a plurality of converter capacitors via a plurality of switches configured to be activated in a first mode of operation;
   periodically supplying charge from said plurality of converter capacitors to said stimulator capacitor via said plurality of switches configured to be activated in a second mode of operation; wherein the relationship between the voltage supplied by the voltage source and the voltage supplied to said stimulator capacitor defines a multiplication factor that is determined by the configuration of switches activated in said first and second modes of operation;
   periodically measuring a voltage across said stimulator capacitor; and
   altering said switches activated in said first and second modes of operations in response to said voltage measured across said stimulator capacitor.

14. The method as in claim 13 further comprising the step of increasing said multiplication factor when said voltage measured across said stimulator capacitor is below a certain threshold voltage.

15. The method as in claim 13 further comprising the step of decreasing said multiplication factor when said voltage measured across said stimulator capacitor is above a threshold voltage.

16. The method as in claim 13 wherein the rate of switching between said first and second modes of operations is adjustable in response to said voltage measured across said stimulator capacitor.

* * * * *